(12) United States Patent
Suzuki et al.

(10) Patent No.: US 6,709,870 B2
(45) Date of Patent: Mar. 23, 2004

(54) SAMPLE EXTRACTING DEVICE AND ADDING DEVICE

(75) Inventors: Motoo Suzuki, Kanagawa (JP); Takashi Ishikawa, Kanagawa (JP); Hirokazu Saito, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 68 days.

(21) Appl. No.: 09/739,327

(22) Filed: Dec. 19, 2000

(65) Prior Publication Data

US 2001/0004449 A1 Jun. 21, 2001

(30) Foreign Application Priority Data

Dec. 20, 1999 (JP) .......................................... 11-361369

(51) Int. Cl.⁷ ................................................. B01L 3/02
(52) U.S. Cl. ...................... 436/49; 436/180; 422/100; 73/864.22; 73/864.24
(58) Field of Search .............. 422/100, 81, 82; 436/49, 180, 52, 53; 73/864.21, 864.22, 864.24, 864.25

(56) References Cited

U.S. PATENT DOCUMENTS

| | | | | |
|---|---|---|---|---|
| 4,015,938 A | * | 4/1977 | Jay | .......................... 73/864.22 |
| 4,323,537 A | * | 4/1982 | Mody | .......................... 422/63 |
| 5,372,782 A | * | 12/1994 | Karkantis et al. | .............. 422/63 |
| 5,730,938 A | * | 3/1998 | Carbonari et al. | |
| 5,827,744 A | * | 10/1998 | Fose et al. | |

FOREIGN PATENT DOCUMENTS

| | | |
|---|---|---|
| JP | 5-141549 | 6/1993 |
| JP | 6-241328 | 8/1994 |

OTHER PUBLICATIONS

Patent Abstract of Japan 05–141549 Jun. 8, 1993.
Patent Abstract of Japan 06–241328 Aug. 30, 1994.

* cited by examiner

Primary Examiner—Jan Ludlow
(74) Attorney, Agent, or Firm—Sughrue Mion, PLLC

(57) ABSTRACT

A sample tube of a sampling valve is moved up and down by a cylinder. When the sample tube is moved downward, a sample inlet opposes a stored sample, and the sample can be extracted. When the sample tube is moved upward, the sample inlet opposes a cleaning liquid path. Thus, cleaning liquid is fed into the cleaning liquid path from a cleaning liquid supply port of a cleaning pipe. The cleaning liquid flows within the sample tube from the sample inlet, and flows out from a sample discharge port. Thus, an entire interior of the sample tube can be cleaned. In a sample extracting device using the sampling valve, a state in which no air or impurities are mixed in the sample can always be maintained, such that stable extraction can be carried out.

20 Claims, 15 Drawing Sheets

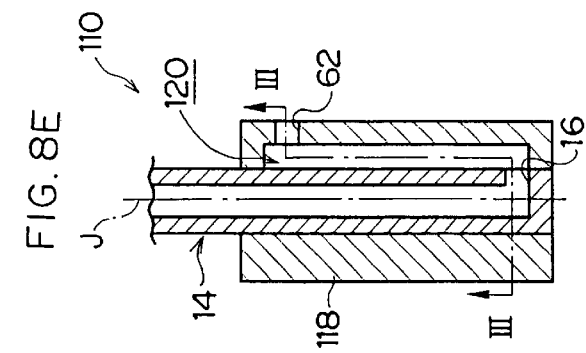
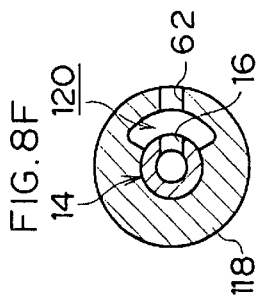
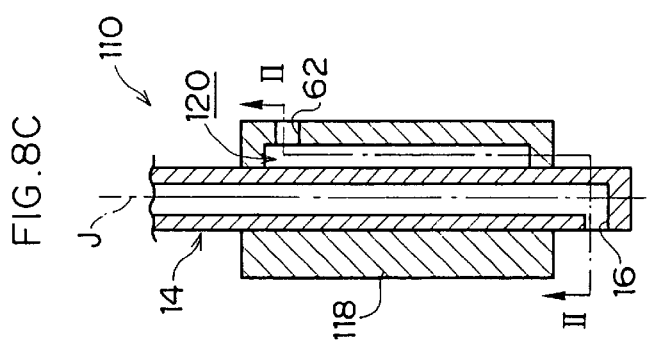
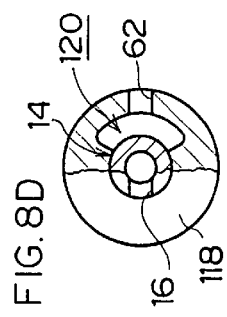
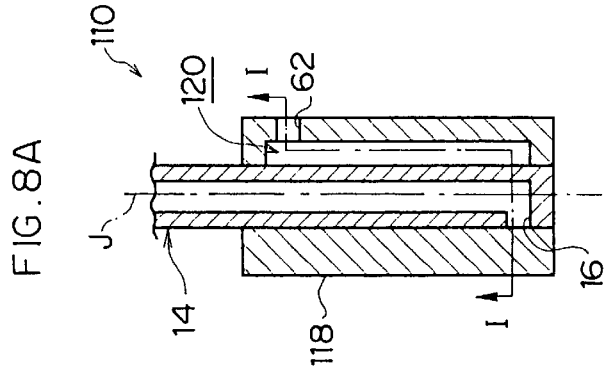
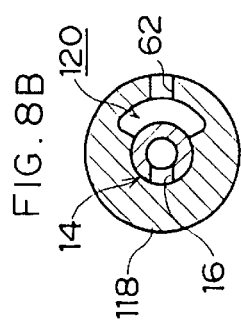

SAMPLE EXTRACTING DEVICE AND ADDING DEVICE

BACKGROUND OF THE INVENTION

1. Field of the Invention

The present invention relates to a sample extracting device and an adding device. In particular, the present invention relates to a valve which can be used as a sampling valve for extracting (sampling) a sample from a sample tank (a sample stock tank, a reaction adjusting tank, a stirring/mixing tank, or the like) used in chemical plants, industrial facilities, experiment facilities, or the like, or which can be used for adding an additive to a sample, and the present invention also relates to a sample extracting device and an adding device using this valve.

2. Description of the Related Art

FIG. 13 illustrates an example of a conventional sampling valve for sampling a sample from a sample tank.

The sample valve is structured such that a T-valve 202 which is formed in a substantial T-shape is provided at the bottom of a tank 200. By opening and closing the T-valve 202 by an actuator 204 or the like, a predetermined amount of the sample can be removed via a pipe 206.

However, in the sampling valve having the structure illustrated in FIG. 13, a liquid flow-out opening 208 of the pipe 206 is disposed lower than the solution surface of the sample in the tank 200. Thus, when the T-valve 202 is opened, the air remaining in the pipe passes through the pipe 206 and enters into the tank 200. If the sample is a liquid, the sample liquid becomes foamy due to the air, which may present problems in using the sample or the like.

Generally, with a sampling valve of this type of structure, it is desirable to appropriately clean the T-valve 202 and the pipe 206. However, when the sample in the tank 200 chemically changes or the state of the sample changes, the interior of the pipe cannot be cleaned quickly after sampling the sample. Thus, it is difficult to carry out sampling continuously in a state in which there are no impurities.

Further, in this sampling valve, structurally, cleaning of the interior of the pipe 206 is difficult, and it is easy for the cleaning liquid to remain in the pipe 206. An additional structure, such as a pipe for guiding the cleaning liquid within the pipe 206 or a valve for starting and stopping supply of the cleaning liquid, must be provided separately, such that the structure becomes complex on the whole, and the cost thereof increases.

FIG. 14 illustrates a conventional sampling valve 230 in which a movable element 234 provided between fixed elements 232, 236 is rotated so as to switch the sampling path, and a predetermined amount of a sample is sampled (see Japanese Patent Application Laid-Open (JP-A) No. 5-141549). With a specific sampling path selected, a corresponding valve 238 is opened and cleaning liquid is sucked in by a suction means 240 so as to be made to flow through and clean the sampling path.

However, in this sampling valve 230 as well, although the selected sampling path is cleaned, a pipette portion 242, whose distal end portion is disposed within the sample liquid, cannot be cleaned unless the sample tube containing the sample is removed. As a result, the sample cannot be sampled for checking changes in the properties over time.

FIG. 15 illustrates a conventional sampling valve 260 (see JP-A-6-241328) which is different than the above-described structures. This sampling valve 260 is provided with a nozzle 264 which forks off from a pipe 262. A predetermined amount of the fluid in the pipe 262 is extracted and used as a sample for testing or the like. The sample valve 260 has a ball valve structure such that even a minute amount of liquid does not remain in the valve at the time of opening and closing, and a circulating piece 265 can be cleaned.

However, as long as the continuously flowing sample exists in the pipe 262, the circulating piece 265 can be cleaned even at the sampling valve 260. However, if a portion of the sampled fluid already remains in the nozzle 264, the interior of the nozzle 264 is not cleaned, and thus, there is the possibility that impurities may remain.

SUMMARY OF THE INVENTION

In view of the aforementioned, an object of the present invention is to provide a valve which enables reliable cleaning of an interior of a sample tube, and a sample extracting and adding device using the valve.

A first aspect of the present invention is a device for extracting a sample from a container, the device comprising: (a) a cleaning tube; and (b) a sample tube having an opening, the sample tube being switchably mounted relative to the cleaning tube, between a sampling position at which the sample tube opening is placed in fluid communication with the environment for contacting a sample in a container, and a cleaning position at which the opening is placed in fluid communication with the cleaning tube for cleaning the sample tube.

The sample tube and the cleaning tube are moved relatively by a moving means. In a state in which the first opening portion is at the sampling position, the stored sample stored in the container flows from the first opening portion into the sample tube and flows to the second opening portion, and the stored sample can be extracted.

The sample tube and the cleaning tube are moved relatively by the moving means. In a state in which the first opening portion is at the cleaning position, the cleaning liquid is injected into the first opening portion from the cleaning tube, and the interior of the sample tube can be cleaned. At this time, the injected cleaning liquid flows out from the second opening portion. Because the cleaning liquid flows from the first opening portion to the second opening portion, the interior of the sample tube, i.e., the entire region over which the sample flows, can be cleaned.

If the cleaning liquid can flow between the first opening portion and the second opening portion, the direction of flow thereof is not particularly limited. Namely, the cleaning liquid may be injected from the second opening portion and discharged from the first opening portion.

Further, it is not only possible for the stored sample to be taken in from the first opening portion and the sample to be extracted from the second opening portion, but also, conversely, the sample may be injected from the second opening portion and added into the container from the first opening portion. In the latter case, the first opening portion does not necessarily have to communicate with the stored sample. For example, the sample may be injected and added into the container from above. Further, a state in which there is no sample in the container (i.e., the container is empty) is also possible.

By moving the sample tube and the cleaning tube relative to one another along the longitudinal direction of the sample tube, the first opening portion can be moved between the sampling position and the cleaning position. Thus, the structure for relatively moving the sample tube and the cleaning tube is simple.

Further, because the cleaning tube is provided integrally with the sample tube, as compared with a case in which the cleaning tube is provided as a member separate from the sample tube and is provided at the exterior of the sample tube, the cleaning tube can be provided and the cleaning liquid can be injected into the sample tube in a smaller space.

A second aspect of the present invention is a device for introducing an additive to a sample in a container, the device comprising: (a) a reservoir for holding an additive for introduction to a sample in a container; (b) a cleaning tube; and (c) a sample tube connected in fluid communication to the reservoir, the sample tube having an opening and being switchably mounted relative to the cleaning tube, between an adding position at which the opening of the sample tube is placed in fluid communication with the environment for introducing the additive to the sample, and a cleaning position at which the opening is placed in fluid communication with the cleaning tube for cleaning the sample tube.

When the first opening portion of the valve is at the sampling position, by supplying the additive to the second opening portion by the additive supplying device, a predetermined amount of the additive can be added to the sample.

When the cleaning liquid is supplied by the cleaning liquid supplying device at the time that the first opening portion of the valve is at the cleaning position, the cleaning liquid is injected through the cleaning tube into the interior of the sample tube and flows out from the second opening portion. In this way, the entire interior of the sample tube, i.e., the entire region over which the additive flows, can be cleaned. Accordingly, when an additive is added again after cleaning, no impurities are mixed therein, and addition can be carried out stably.

Further, the cleaning liquid supplied by the cleaning liquid supplying device is injected into the sample tube from the second opening portion, and flows out into the cleaning tube from the first opening portion which is at the cleaning position.

A third aspect of the present invention is a method of extracting a sample, comprising the steps of: (a) supplying a sample to a sample tube through a first sample tube opening; (b) discharging the sample from a second sample tube opening; (c) connecting the first sample tube opening to a cleaning tube by moving the sample tube and cleaning tube relative to one another; (d) supplying a cleaning agent to the sample tube from the cleaning tube through the first sample tube opening; and (e) contacting the sample with the first sample tube opening by moving the sample tube and cleaning tube relative to one another.

When the first opening portion of the valve is at the sampling position, by removing the stored sample from the second opening portion by the extracting device, a predetermined amount of the sample can be extracted.

Further, when the first opening portion of the valve is at the cleaning position, when the cleaning liquid is supplied by the cleaning liquid supplying device, the cleaning liquid is injected through the cleaning tube into the sample tube, and flows out from the second opening portion. In this way, the interior of the sample tube, i.e., the entire region over which the sample flows can be cleaned. Accordingly, when a sample is extracted after cleaning, air or impurities are not mixed therein, and thus, extraction can be carried out stably.

The cleaning liquid supplied by the cleaning liquid supplying device is injected into the interior of the sample tube from the second opening portion, and flows out into the cleaning tube from the first opening portion which is at the cleaning position.

BRIEF DESCRIPTION OF THE DRAWINGS

FIG. 8A is a cross-sectional view illustrating a portion of a sampling valve of a second embodiment of the present invention.

FIG. 8B is a cross-sectional view taken along line I—I of FIG. 8A.

FIG. 8C is a cross-sectional view illustrating a portion of the sampling valve of the second embodiment of the present invention in a sampling state.

FIG. 8D is a cross-sectional view taken along line II—II of FIG. 8C.

FIG. 8E is a cross-sectional view illustrating a portion of the sampling valve of the second embodiment of the present invention in a cleaning state.

FIG. 8F is a cross-sectional view taken along line III—III of FIG. 8E.

DESCRIPTION OF THE PREFERRED EMBODIMENTS

Figure 1:
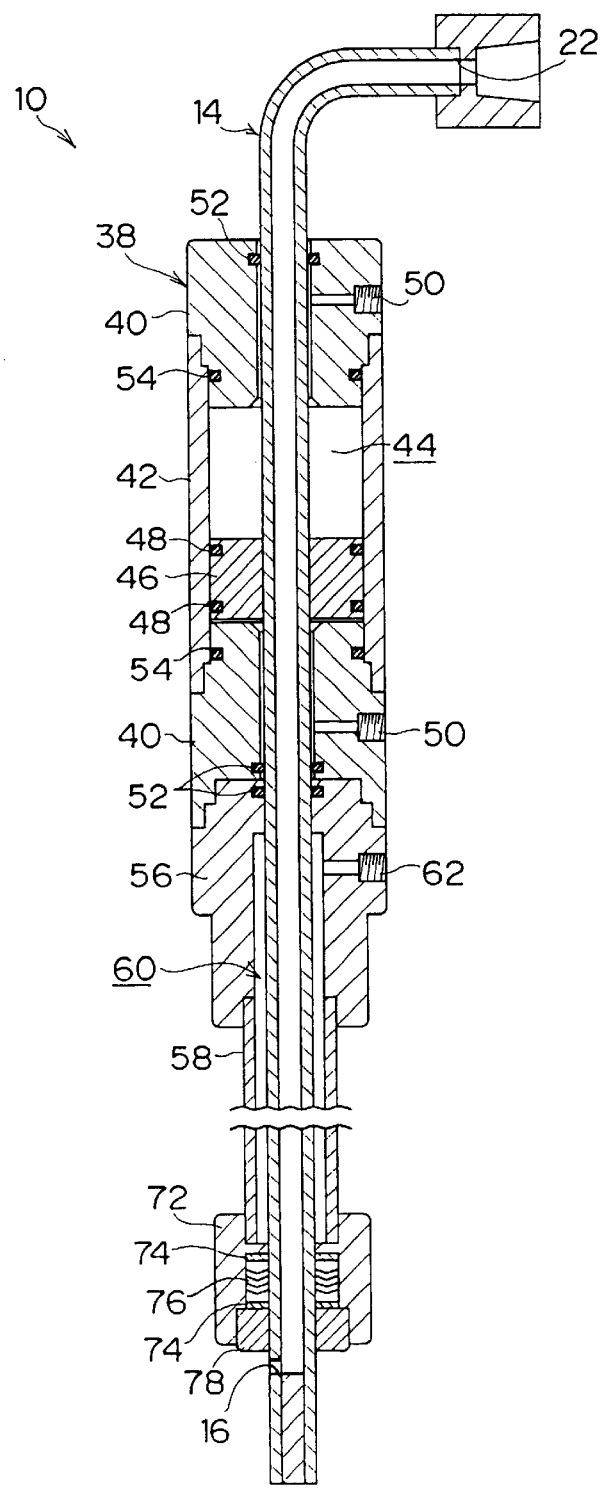
FIG. 1 is a cross-sectional view illustrating a sampling valve of a first embodiment of the present invention in a sampling state.
Figure 2:
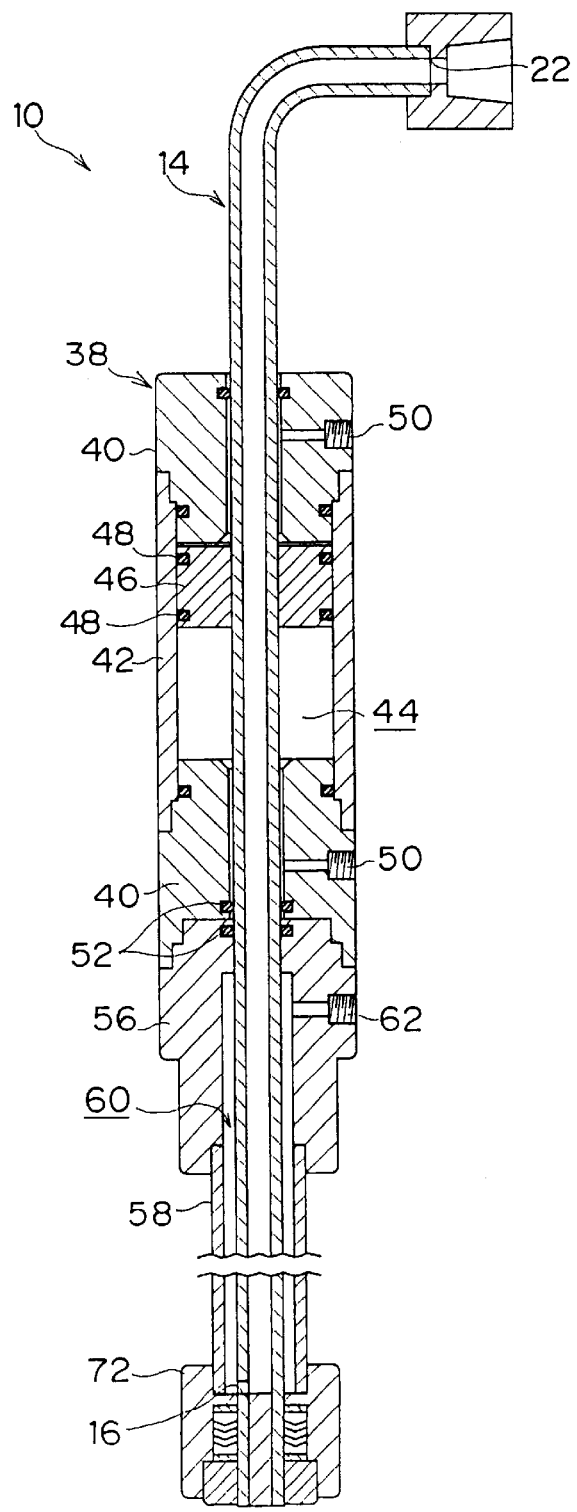
FIG. 2 is a cross-sectional view illustrating the sampling valve of the first embodiment of the present invention in a cleaning state.
Figure 3:
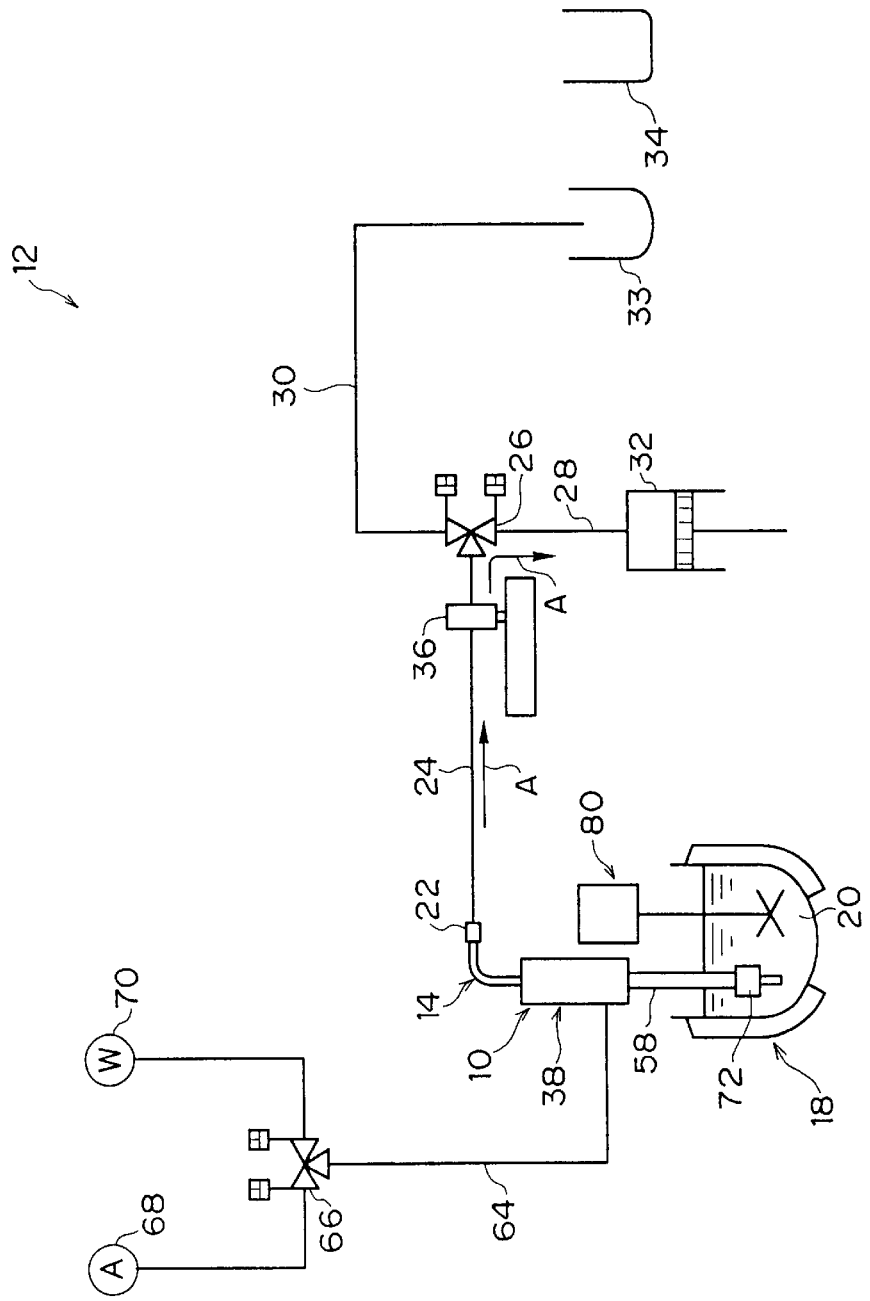
FIG. 3 is a schematic structural view illustrating a sample extracting device of the first embodiment of the present invention.

FIGS. 1 and 2 illustrate a sampling valve 10 relating to an embodiment of the present invention. FIG. 3 illustrates a sample extracting device 12 which is equipped with the sampling valve 10.

As illustrated in FIGS. 1 and 2, the sampling valve 10 has a sample tube 14 which is formed so as to be substantially tubular. The bottom end of the sample tube 14 is sealed, and a sample intake 16 is disposed directly above the sealed portion. As illustrated in FIG. 3, the lower portion of the sample tube 14 is disposed within a stored sample 20 of liquid stored in a sample tank 18. A predetermined amount of the sample is extracted (i.e., sampled) from the stored sample 20 by the sample extracting device 12.

The upper end of the sample pipe 14 is a sample outlet 22. As illustrated in FIG. 3, one end of an extracting pipe 24 is connected to the sample outlet 22. The other end of the extracting pipe 24 is connected to a three way valve 26. A suction pipe 28 and a discharge pipe 30 are also connected to the three way valve 26. By operating the three way valve 26, the extracting pipe 24 can be made to communicate with either the suction pipe 28 or the discharge pipe 30.

A suction device 32 is provided at the distal end of the suction pipe 28. By driving the suction device 32 in a state in which the extracting pipe 24 and the suction pipe 28 are communicated, the sample is sucked from the sampling valve 10. On the other hand, an extracted sample container 33, into which the extracted sample is discharged, and a cleaning liquid discharge tank 34, into which cleaning liquid is discharged, are provided at the distal end side of the discharge pipe 30. By moving the discharge pipe 30, the sample can be discharged to the extracted sample container 33 or the cleaning liquid can be discharged to the cleaning liquid discharge tank 34 as will be described later.

A fluid detecting sensor 36 is provided at an intermediate portion of the extracting pipe 24. Due to the sample sucked from the sample tube 14 by the suction device 32 being sensed and suction being stopped, a fixed amount of the sample can be sucked. The fluid detecting sensor 36 may be an ultrasonic sensor, a microwave sensor, or the like.

As illustrated in FIGS. 1 and 2, a cylinder 38 is provided substantially at the longitudinal direction center of the sample tube 14. The cylinder 38 includes a pair of cylinder covers 40 disposed at the longitudinal direction ends of the cylinder 38, and a cylinder pipe 42 provided between the cylinder covers 40. A moving space 44 is formed between the sample tube 14, the cylinder covers 40 and the cylinder pipe 42. A piston 46 fixed to the sample tube 14 is accommodated within the moving space 44. Piston packings 48 are mounted to the outer periphery of the piston 46. The piston packings 48 prevent air from flowing between the outer surface of the piston 46 and the inner surface of the cylinder pipe 42, and enable sliding of the piston 46 along the inner surface of the cylinder pipe 42.

A port 50 for supplying air for driving is formed at each of the cylinder covers 40. Air for driving can be supplied into the moving space 44 from a device for supplying air for driving (not shown) by selecting one of the ports 50 for supplying air for driving. The air for driving supplied from the port 50 for supplying air for driving passes through the space formed between the cylinder cover 40 and the sample tube 14 and enters into the moving space 44. As illustrated in FIG. 2, when the piston 46 is at the upper cylinder cover 40 side, when air for driving is supplied from the port 50 for supplying air for driving of the upper cylinder cover 40, the piston 46 is pushed by the air for driving and moves downward, and the sample tube 14 also moves downward. Conversely, when the piston 46 is at the lower cylinder cover 40 side as shown in FIG. 1, when air for driving is supplied from the port 50 for supplying air for driving of the lower cylinder cover 40, the piston 46 is pressed by the air for driving and moves upward, and the sample tube 14 also moves upward. This upward and downward movement is limited to a fixed range due to the piston 46 abutting the cylinder covers 40. Note that an air actuator, which is one example of the moving means of the present invention, is formed by the cylinder 38 and the device for supplying air for driving.

Leaking of the air for driving in a direction opposite to the direction of the moving space 44 from the ports 50 for supplying air for driving through the spaces between the cylinder covers 40 and the sample tube 14, is prevented by rod packings 52 provided between the cylinder covers 40 and the sample tube 14. Similarly, leaking of the air for driving from the moving space 44 through the space between the cylinder covers 40 and the cylinder pipe 42, is prevented by O-rings 54 provided between the cylinder covers 40 and the cylinder pipe 42.

A cleaning pipe 58 is provided beneath the cylinder 38 via a cleaning pipe holder 56. The cleaning pipe 58 is formed in a tube-shape having an internal diameter which is greater than the outer diameter of the sample tube 14. The cleaning pipe 58 is disposed coaxially with the sample tube 14 and is wound around the sample tube 14 from the outer side thereof. A cleaning liquid path 60, which is tubular and through which cleaning liquid flows, is formed between, on the one hand, the outer surface of the sample tube 14, and on the other hand, the inner surface of the cleaning pipe 58 and the inner surface of the cleaning pipe holder 56.

A cleaning liquid supply port 62, through which cleaning liquid is supplied to the cleaning liquid path 60, is formed in the cleaning pipe holder 56. As illustrated in FIG. 3, one end of a cleaning liquid supply pipe 64 is connected to the cleaning liquid supply port 62 (see FIG. 1). The other end of the cleaning liquid supply pipe 64 is connected to a three way valve 66. An air compressor 68 and a cleaning liquid supply device 70 are also connected to the three way valve 66. By operating the three way valve 66, one of cleaning liquid and compressed air is fed into the cleaning liquid path 60 from the cleaning liquid supply port 62 via the cleaning liquid supply pipe 64. The specific structure of the cleaning liquid supply device 70 is not limited. For example, the cleaning liquid supply device may be structured by a cleaning liquid tank which accommodates cleaning liquid, and a pump provided at the cleaning liquid tank.

As illustrated in FIGS. 1 and 2, a seal case 72 is provided at the lower portion of the cleaning pipe 58. A packing 76 or a lip seal, a ground seal or the like is held by adapters 74 within the seal case 72. A packing presser 78 is mounted therebeneath. Examples of the packing 76 are a lip seal, a ground seal, V-packing or the like. As illustrated in FIG. 1, in a state in which the sample tube 14 is positioned at the lowermost position, the sample intake 16 is disposed at a position lower than the packing presser 78. The packing presser 78 is formed in a predetermined configuration such that the sample intake 16 at this time communicates with the stored sample 20 (see FIG. 3) in the sample tank 18. (This position is the sampling position.) Further, the V-packing 76 seals the space between the cleaning pipe 58 and the sample tube 14, such that the sample tube 14 is movable between the position illustrated in FIG. 1 and the position illustrated in FIG. 2 at which the sample tube 14 is moved to the uppermost position, and such that the cleaning liquid or the compressed air within the cleaning liquid path 60 does not flow out into the stored sample 20 or conversely the stored sample 20 does not flow into the cleaning liquid path 60 due to movement of the sample tube 14.

The length of the sample tube 14 is a predetermined length which is such that, when the sample tube 14 is disposed at the uppermost position as illustrated in FIG. 2, the sample intake 16 communicates with the cleaning liquid path 60. (This position is the cleaning position.)

Next, operation of the sampling valve 10 and the sample extracting device 12 of the present first embodiment will be described.

When the stored sample 20 is to be extracted from the sample tank 18 of FIG. 3, as illustrated in FIG. 1, the air for driving is supplied from the port 50 for supplying air for driving of the upper cylinder cover 40 of the cylinder 38, and the sample tube 14 is moved downward. In this way, the sample intake 16 opposes the stored sample 20 (see FIG. 3). (This is the sampling position.) Then, the three way valve 26 is operated such that the extracting pipe 24 and the suction pipe 28 are made to communicate with one another.

When the suction device 32 is driven in this state, as illustrated by arrows A in FIG. 3, the stored sample 20 within the sample tank 18 is sucked from the sample intake 16 (see FIG. 1). By stopping the sucking by the suction device 32 when the sucked sample has reached the fluid detecting sensor 36, a predetermined amount of sample is extracted.

Next, as illustrated in FIG. 2, air for driving is supplied from the lower port 50 for supplying air for driving, and the sample tube 14 is moved upward. In this way, the sample intake 16 is moved to the cleaning position, and communicates with the cleaning liquid path 60. Here, the three way valve 26 is switched such that the extracting pipe 24 and the discharge pipe 30 are communicated. Further, the three way valve 66 is operated, and compressed air is fed into the sampling valve 10 from the air compressor 68.

Figure 4:
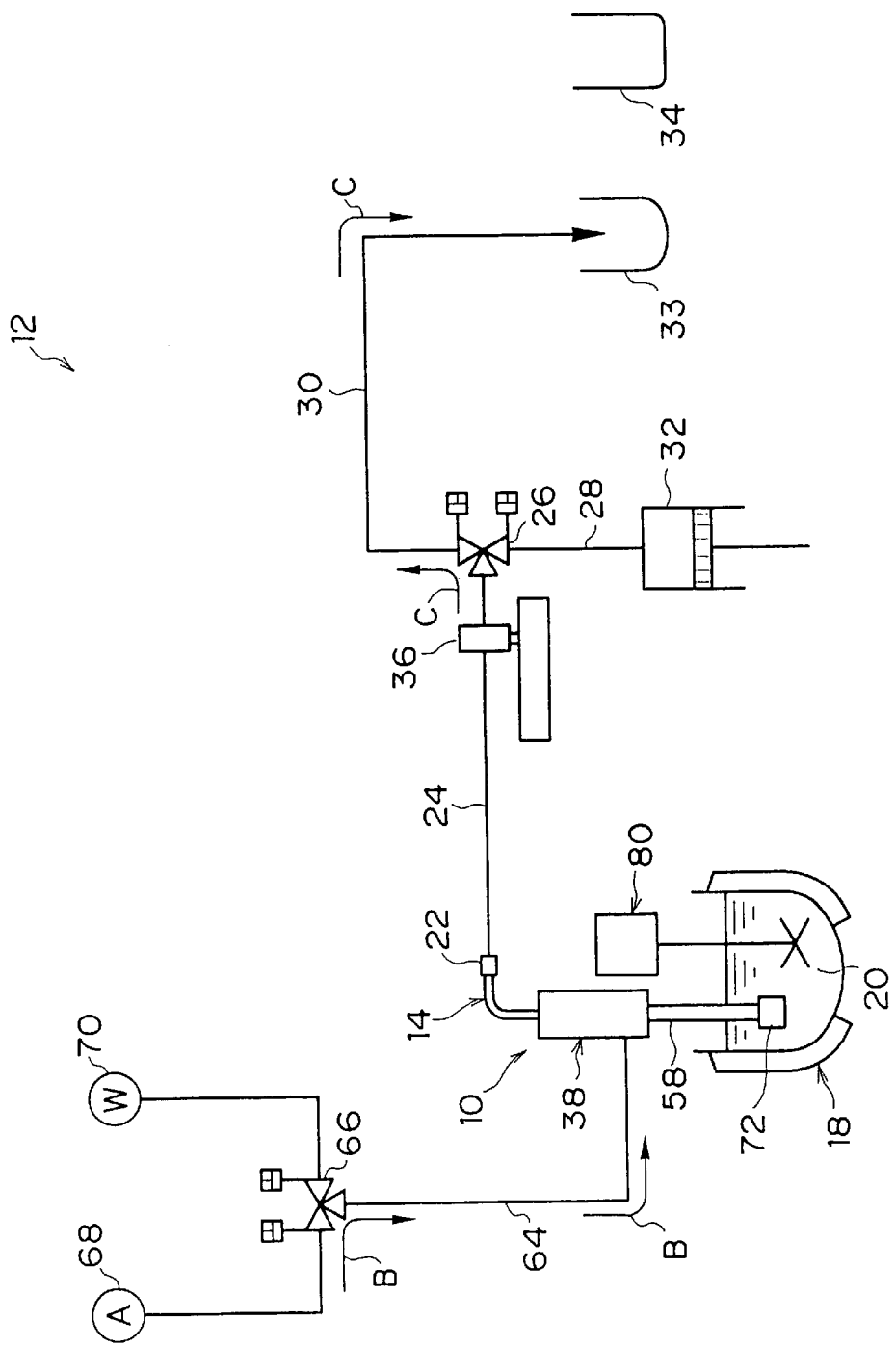
FIG. 4 is a schematic structural view illustrating the sample extracting device of the first embodiment of the present invention.

In this state, the compressor 68 is driven, and compressed air is fed into the cleaning liquid path 60 (see FIG. 2) from the cleaning liquid supply port 62 as illustrated by arrows B in FIG. 4. Due to the compressed air, as illustrated by arrows C, the predetermined amount of the sample existing in the sampling valve 10 and the extracting pipe 24 is pushed out, and is discharged into the extracted sample container 33.

Figure 5:
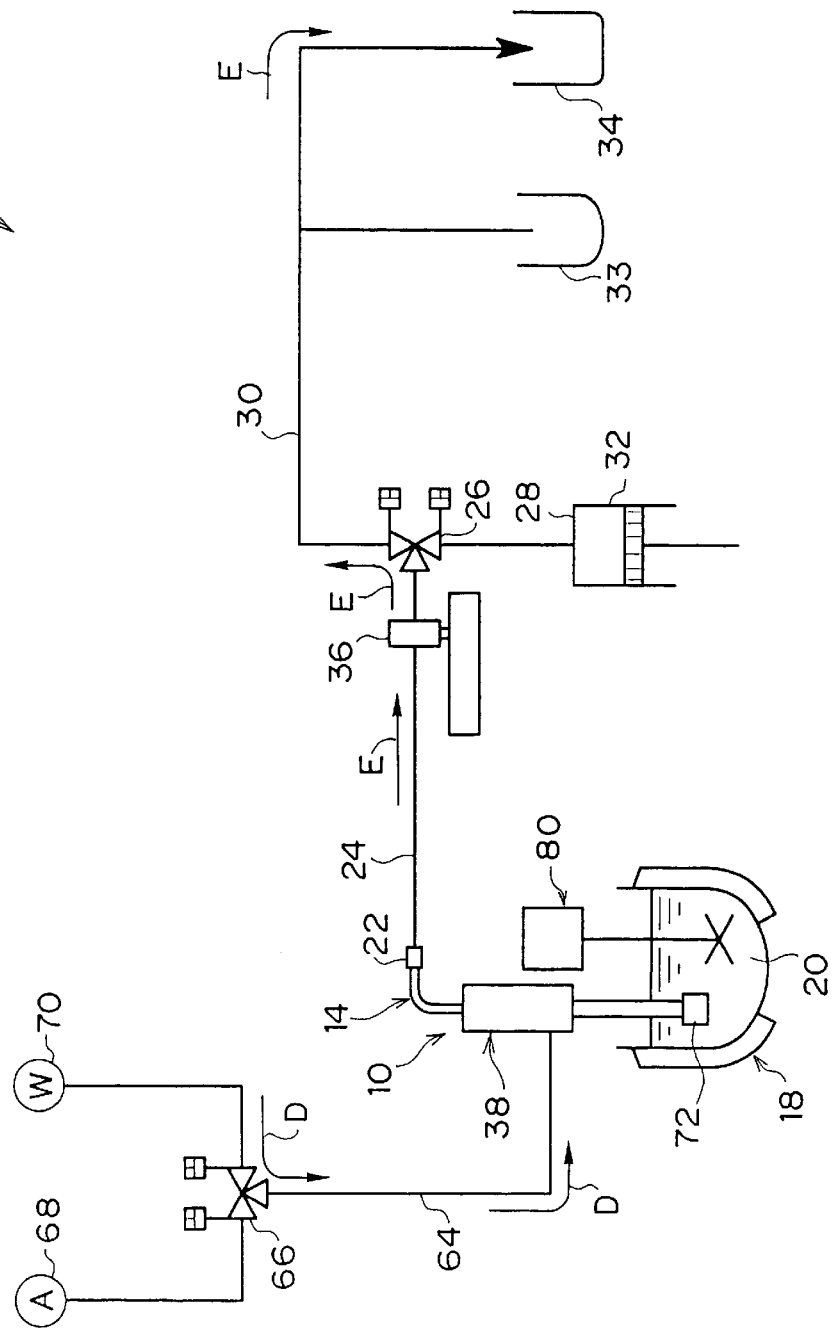
FIG. 5 is a schematic structural view illustrating the sample extracting device of the first embodiment of the present invention.

After extraction has been completed, as illustrated in FIG. 5, the discharge pipe 30 is moved from the extracted sample container 33 to the cleaning liquid discharge tank 34. Then, the three way valve 66 is switched, and cleaning liquid is fed into the sampling valve 10 from the cleaning liquid supply device 70.

In this state, when the cleaning liquid supply device 70 is driven and the cleaning liquid is fed into the cleaning liquid path 60 from the cleaning liquid supply port 62 as shown by arrows D, the cleaning liquid flows into the sample tube 14 from the sample intake 16 (see FIG. 2), and flows through the interior of the sample tube 14 and out from the sample outlet 22. In this way, because the cleaning liquid flows through the entire interior of the sample tube 14, the entire interior of the sample tube 14 is cleaned. The cleaning liquid discharged from the sample outlet 22 is, as illustrated by arrows E in FIG. 5, discharged through the extracting pipe 24 and the discharge pipe 30 into the cleaning liquid discharge tank 34.

Figure 6:
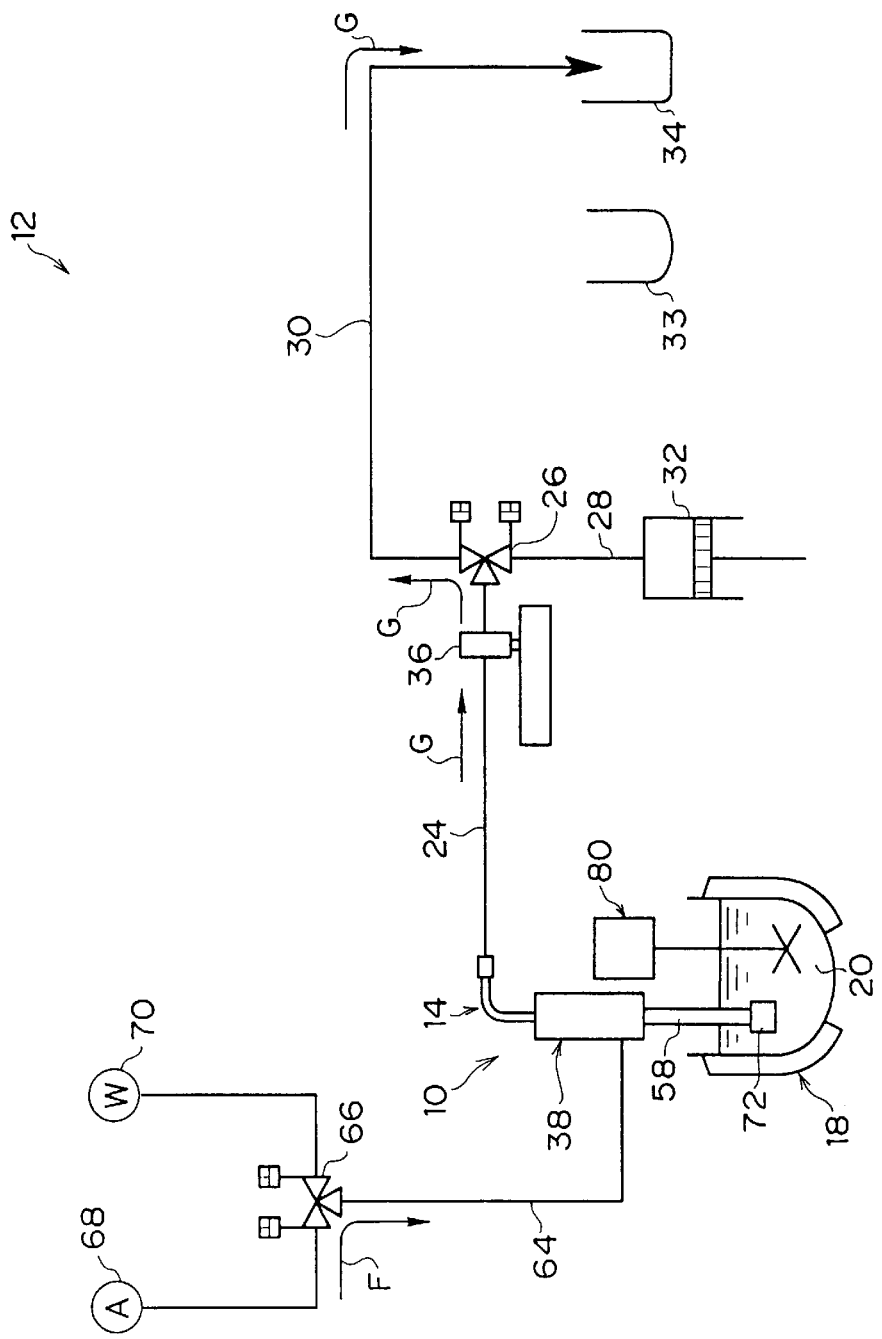
FIG. 6 is a schematic structural view illustrating the sample extracting device of the first embodiment of the present invention.

After cleaning has been completed, when the three way valve 66 is switched and the air compressor 68 is driven such that compressed air is fed to the sampling valve 10 from the air compressor 68, the compressed air fed from the air compressor 68 is fed into the cleaning liquid path 60 from the cleaning liquid supply port 62 and into the sample tube 14, as illustrated by arrow F in FIG. 6. The compressed air flows into the sample tube 14, and as illustrated by arrows G in FIG. 6, flows from the sample outlet 22 through the extracting pipe 24 and the discharge pipe 30, and is discharged into the cleaning liquid discharge tank 34. The fluid remaining in the sample tube 14 is forced out by the compressed air such that the cleaning liquid remaining on the inner surface of the sample tube 14 is removed.

Figure 7:
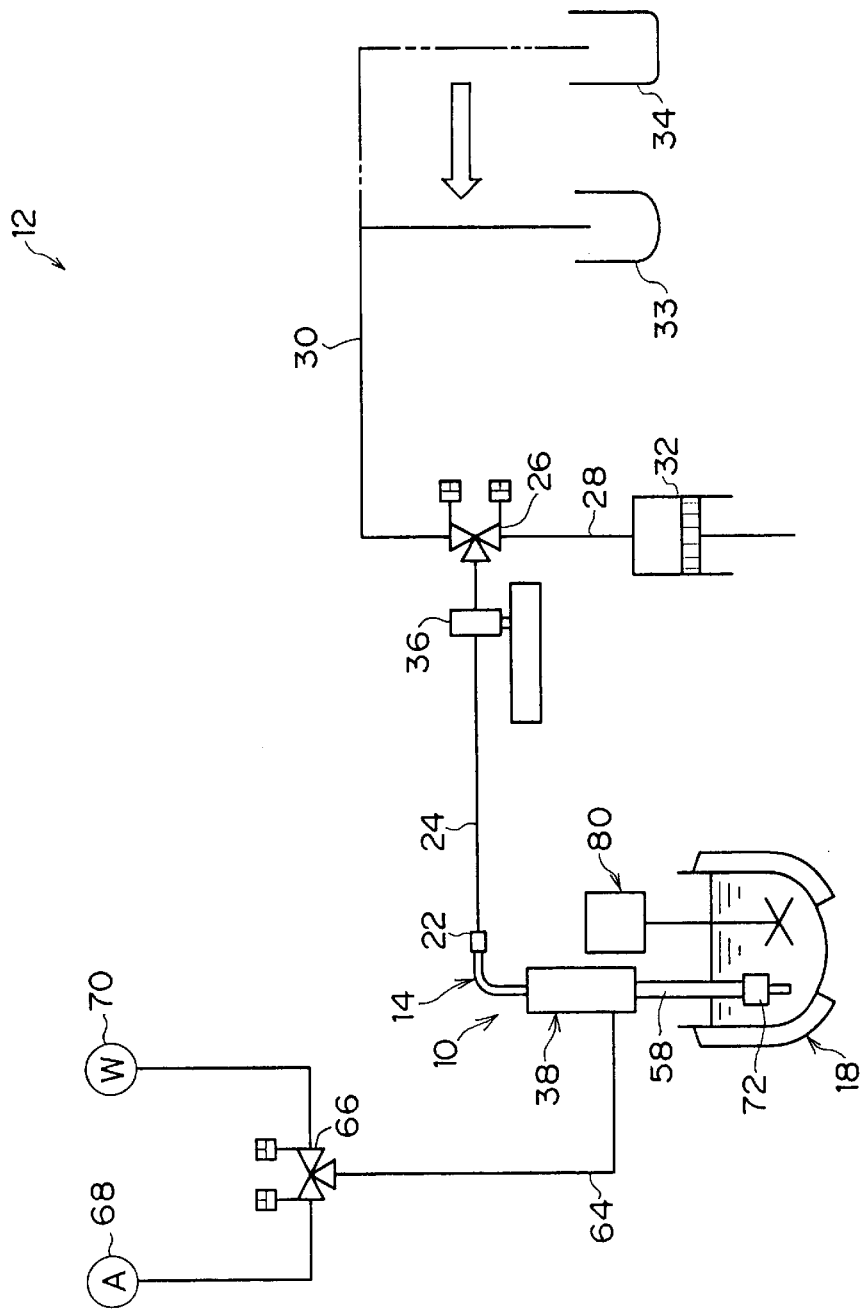
FIG. 7 is a schematic structural view illustrating the sample extracting device of the first embodiment of the present invention.

After the fluid has been removed as described above, as illustrated in FIG. 7, the discharge pipe 30 is moved to the extracted sample container 33 which holds the extracted sample. Further, after the three way valve 26 is opened and the suction device 32 is returned to its original state, the three way valve 26 is closed. Moreover, the sample tube 14 is moved downward.

In this way, at the sampling valve 10 of the present first embodiment, the entire interior of the sample tube 14 from the sample intake 16 to the sample outlet 22, i.e., the entire portion through which the sample passes, can be cleaned by the cleaning liquid. As a result, in the sample extracting device 12 using the sampling valve 10, when extraction is to be carried out again after cleaning, a state in which no air or impurities are mixed in the sample can always be maintained, and stable extraction can be carried out.

FIGS. 8A through 8F illustrate portions of a sampling valve 110 of a second embodiment of the present invention. Because the sampling valve 110 is structured substantially the same as the sampling valve 10 of the first embodiment, only the different portions will be explained, and description of the portions which are the same will be omitted. Further, the extracting device of the second embodiment is structured the same as that of the first embodiment, other than the fact that the sampling valve 110 is used in place of the sampling valve 10.

In the sampling valve 110 of the second embodiment, the sample tube 14 moves in the longitudinal direction, and is rotatable by a predetermined angle (e.g., 180° in the present embodiment) around a central line J of the sample tube 14. This rotation may be made possible by providing a motor or the like at the sample tube 14, but rotating of the sample tube 14 is not limited to rotation by a motor.

As illustrated in FIG. 8B, a cleaning pipe 118 has a configuration such that a cleaning liquid path 120 having a substantially fan-shaped cross-section is formed between the cleaning pipe 118 and the sample tube 14. The cleaning liquid supplying port 62 for supplying cleaning liquid is formed at the cleaning liquid path 120.

In the sampling valve 110 of the present second embodiment which has such a structure, when the stored sample is extracted, as illustrated in FIGS. 8C and 8D, the sample tube 14 is moved downward such that the sample intake 16 communicates with the stored sample.

During cleaning of the interior of the sample tube 14 and when fluid is to be removed from the interior of the sample tube 14, as illustrated in FIGS. 8E and 8F, the sample tube 14 is moved upward and rotated around the central line J such that the sample intake 16 and the cleaning liquid path 60 communicate with each other.

Accordingly, in the sampling valve 110 of the present second embodiment, in the same way as the sampling valve 10 of the first embodiment, the entire portion through which the sample passes from the sample intake 16 to the sample outlet 22 (see FIGS. 1 and 2) can be cleaned by the cleaning liquid.

Figure 9:
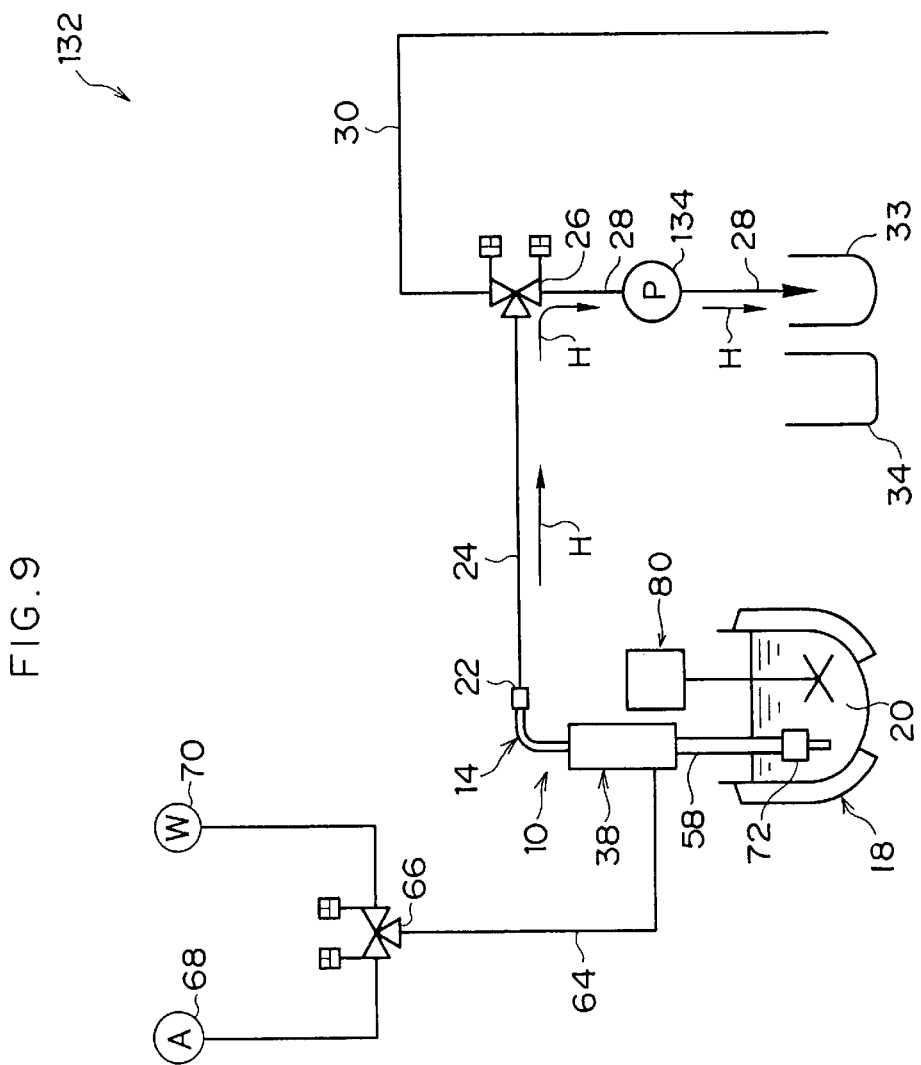
FIG. 9 is a schematic structural view illustrating a sample extracting device of a third embodiment of the present invention.

FIG. 9 illustrates a sample extracting device 132 of a third embodiment of the present invention. The sample extracting device 132 is structured substantially the same as the sample extracting device 12 of the first embodiment. However, in place of the suction device 32 of the first embodiment, a pump 134 is provided at an intermediate portion of the suction pipe 28. Further, the extracted sample container 33 and the cleaning liquid discharge tank 34 are selectably provided at the distal end side of the suction pipe 28. Note that the distal end side of the discharge pipe 30 is open.

Either the sampling valve 10 of the first embodiment or the sampling valve 110 of the second embodiment can be used in the sample extracting device 132 of the present third embodiment, and which of these two sampling valves is used is not particularly limited. In FIG. 9, as one example, the sampling valve 10 of the first embodiment is used.

Other structures are the same as those of the sample extracting device 12 of the first embodiment.

When a sample is extracted by using the sample extracting device 132 of the third embodiment which is structured in this way, the sample intake 16 is set at the sampling position (see FIG. 1), and the three way valve 26 is operated such that the extracting pipe 24 and the suction pipe 28 are communicated.

When the pump 134 is operated in this state, as shown by arrows H in FIG. 9, the stored sample 20 within the sample tank 18 is sucked out from the sample intake 16 (see FIG. 1), and the sucked out sample is discharged into the extracted sample container 33. Driving of the pump 134 is stopped at the point in time when the predetermined amount of sample is extracted. In the same way as the extracting device 12 of the first embodiment, the sucking of the predetermined amount of the sample may be sensed by providing a liquid detecting sensor at an intermediate portion of the extracting pipe 24, or, for example, by sensing the amount of time over which the pump 134 has been driven.

Figure 10:
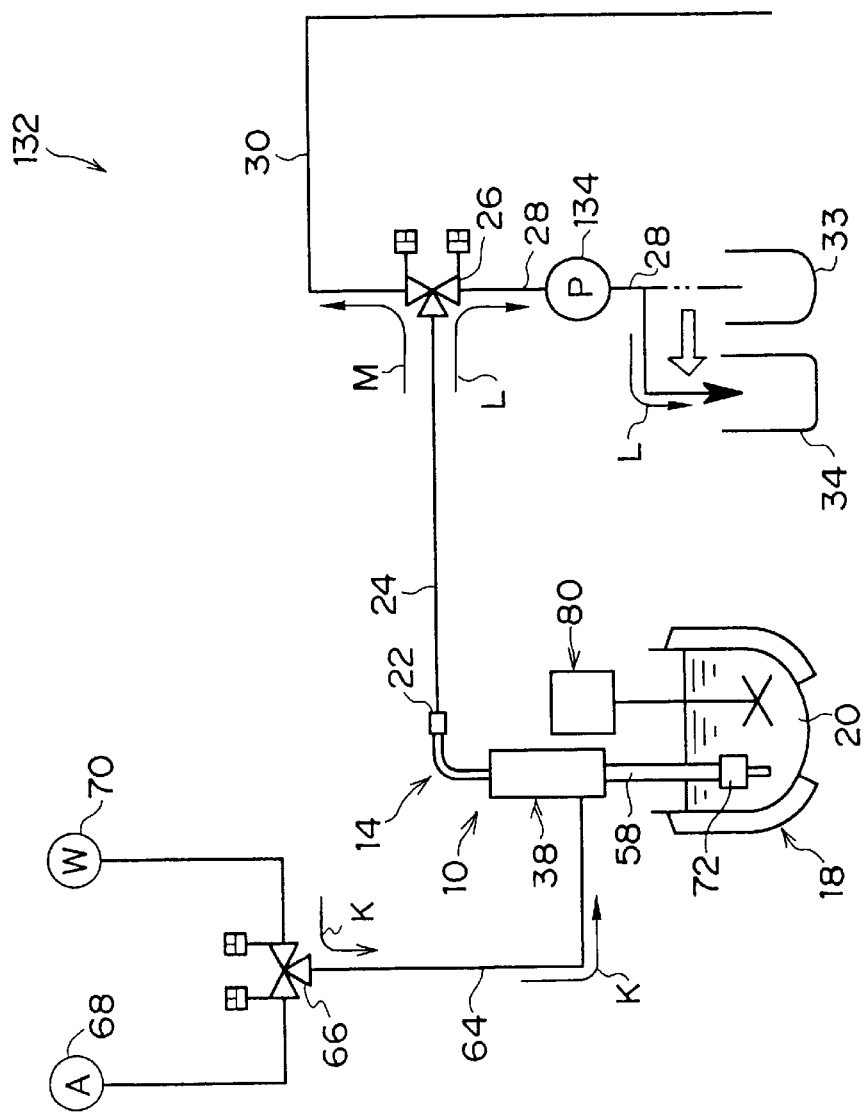
FIG. 10 is a schematic structural view illustrating the sample extracting device of the third embodiment of the present invention.

Next, the sample inlet is set at the cleaning position (see FIG. 2), and as illustrated in FIG. 10, the suction pipe 28 is moved to the cleaning liquid discharge tank 34. Further, when the three way valve 66 is operated and the cleaning liquid supplying device 70 is driven such that cleaning liquid is fed to the sampling valve 10 from the cleaning liquid supplying device 70 and the cleaning liquid is fed into the cleaning liquid path 60 (se FIG. 2) from the cleaning liquid supplying port 62 as illustrated by arrows K, the cleaning liquid flows into the sample tube 14 and flows out from the sample outlet 22. In this way, because the cleaning liquid flows through the entire interior of the sample tube 14, the entire interior of the sample tube 14 is cleaned. Due to the driving of the pump 134, as shown by arrows L in FIG. 10, the cleaning liquid flows from the sample outlet 22 through the extracting pipe 24 and the discharge pipe 30, and is discharged into the cleaning liquid discharge tank 34. Note that, as illustrated by arrow M in FIG. 10, the cleaning liquid may be discharged from the discharge pipe 30 by operating the three way valve 26 so as to make the extracting pipe 24 and the discharge pipe 30 communicate with each other.

Figure 11:
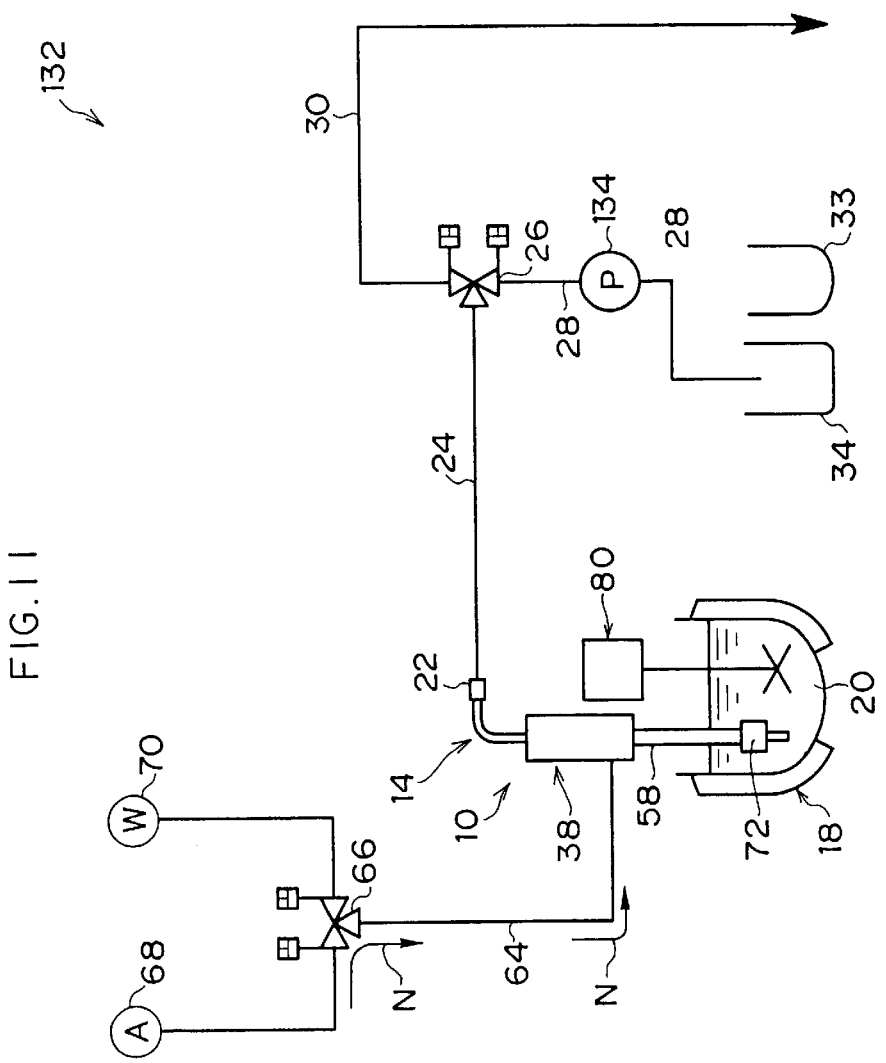
FIG. 11 is a schematic structural view illustrating the sample extracting device of the third embodiment of the present invention.

After cleaning has been completed, when the three way valve 66 is switched and the air compressor 68 is driven such that compressed air is fed from the air compressor 68 into the sampling valve 10, as illustrated by the arrows N in FIG. 11, the compressed air fed from the air compressor 68 flows into the cleaning liquid path 60 (see FIG. 2) from the cleaning liquid supplying port 62, and then flows into the interior of the sample tube 14. Due to the compressed air, the liquid within the sample tube 14 is removed, and adhesion of the cleaning liquid to the inner surface of the sample tube 14 is eliminated. After this removal of the liquid, the compressed air may be discharged from the discharge pipe 30. Alternatively, the three way valve 26 may be operated such that the extracting pipe 24 and the suction pipe 28 are communicated, and the compressed air may be discharged into the cleaning liquid discharge tank 34.

Figure 12:
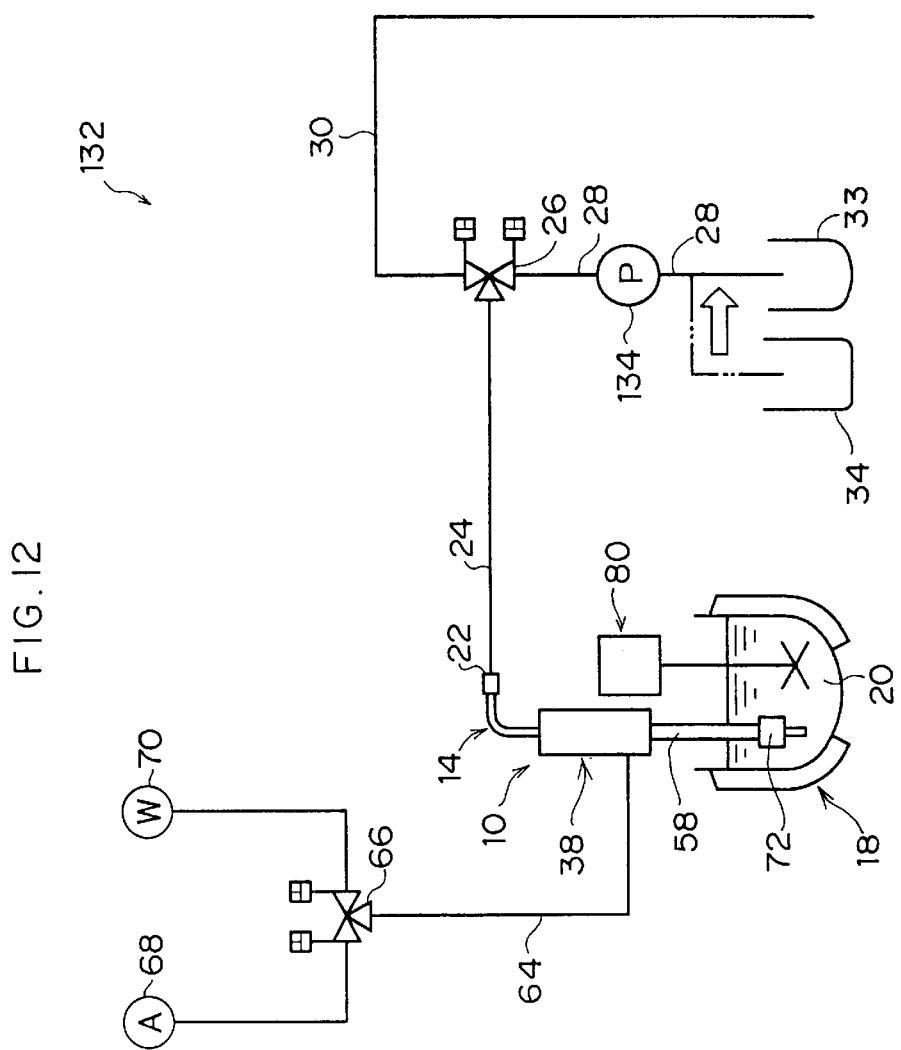
FIG. 12 is a schematic structural view illustrating the sample extracting device of the third embodiment of the present invention.
Figure 13:
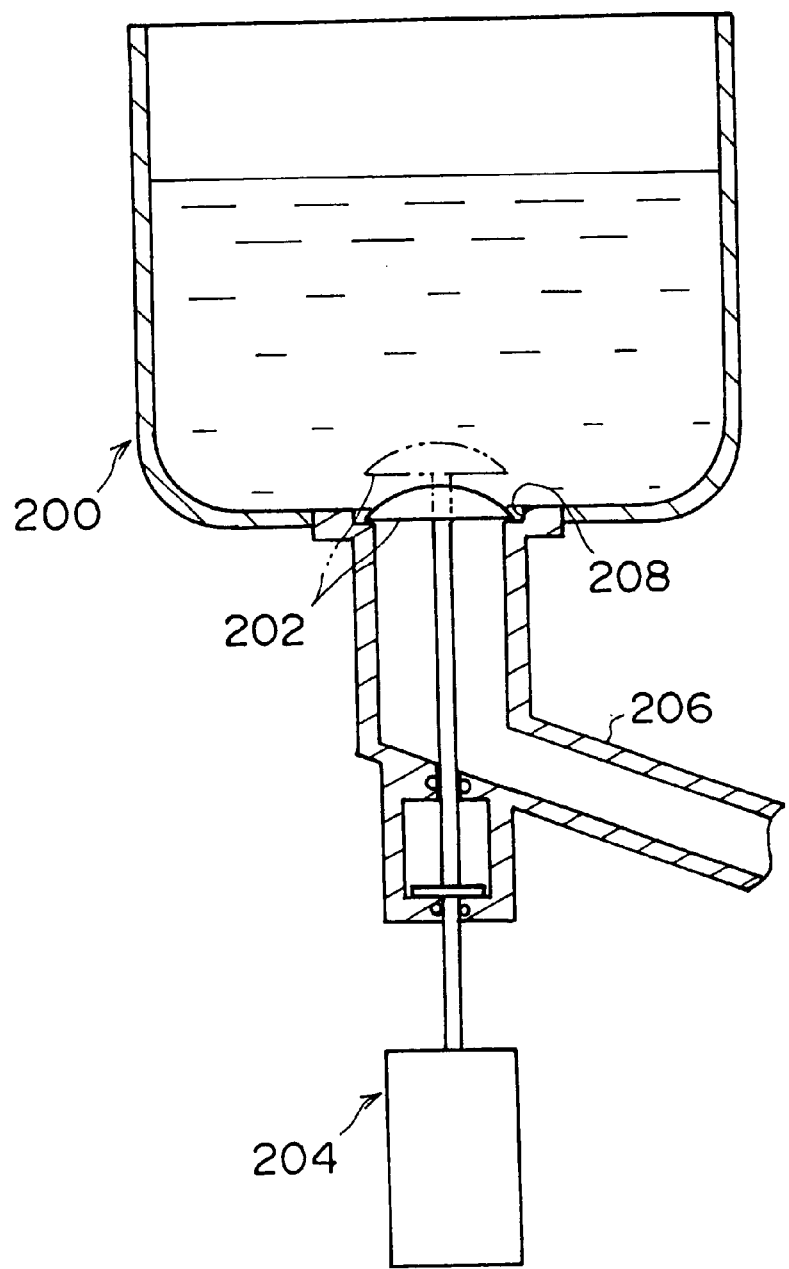
FIG. 13 is a cross-sectional view illustrating a conventional sampling tube.
Figure 14:
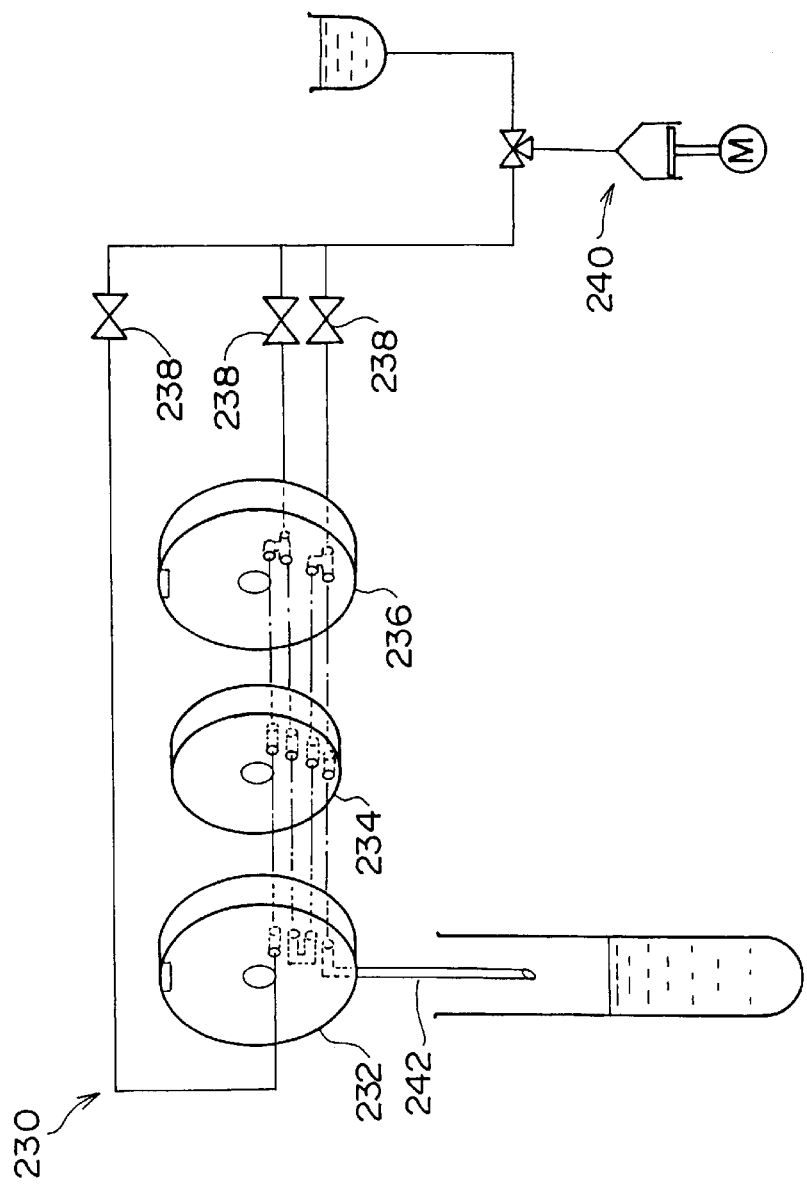
FIG. 14 is a cross-sectional view illustrating a conventional sampling tube.
Figure 15:
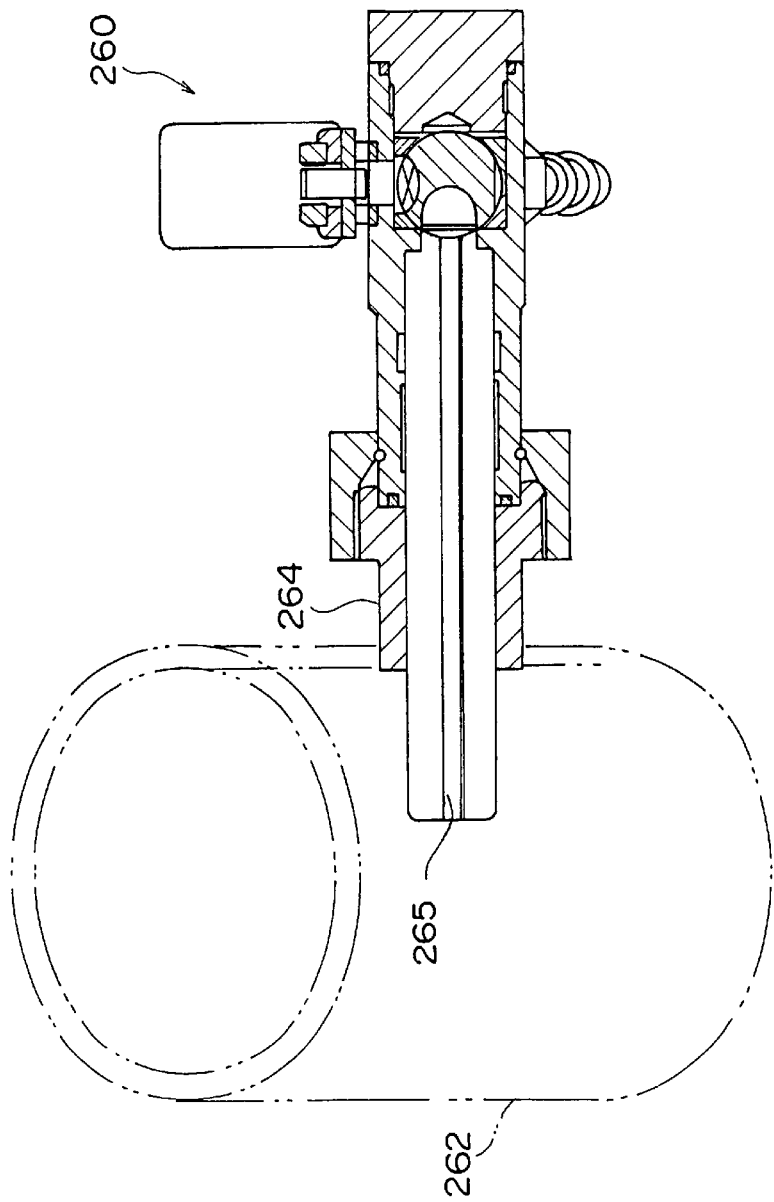
FIG. 15 is a cross-sectional view illustrating a conventional sampling tube.

After the liquid has been removed, as illustrated in FIG. 12, the suction pipe 28 is moved to the extracted sample container 33 side.

In this way, in the sample extracting device 132 of the present third embodiment as well, the entire sampling valve 10 from the sample intake 16 to the sample outlet 22, i.e., all of the portion through which the sample passes, can be cleaned by the cleaning liquid. Thus, after cleaning of the sampling valve 10, when a sample is extracted by using the sample extracting device 132, a state in which air or impurities is not mixed in the sample can always be maintained, and stable extraction can be carried out.

In the above description, cases in which the sampling valves and the sample extracting device are used for extraction of a sample are described. However, the sampling valve and the sample extracting device are not limited to such use.

For example, the extracting device may be used as an adding device for supplying a predetermined amount of an additive into the sample tank. Or, the extracting device may be used as an extracting and adding device which can both extract a sample and supply an additive.

In this case, for example, in the sample extracting device 132 of the third embodiment, an additive may be added into the sample tank 18 as follows. The additive is placed in the sample container 33, the distal end of the suction pipe 28 is disposed within the sample in the sample container 33, and the pump 34 is driven reversely.

In this case, it is not absolutely necessary to provide the sample inlet within the stored sample. As illustrated in FIG. 3 and FIG. 9, when a sample tank 18 provided with a stirring device 80 for stirring the contents within the sample tank 18 is utilized, the additive can be added in the liquid in a vicinity of the stirrer without contaminants being mixed in, and the efficiency of mixing the added, injected liquid can be improved. Thus, such a structure is preferable.

In the above description, in order to move the sample inlet of the sample tube between a position opposing the sample and a cleaning position, the cleaning pipe is fixed and the sample tube is moved. However, it suffices for the sample tube and the cleaning pipe to be able to be moved relative to one another and for the sample inlet to be moved between the sampling position and the cleaning position. For example, the sample tube may be fixed and the cleaning pipe be movable, or the sample tube and the cleaning pipe may both be movable.

Further, the directions of relative movement of the sample tube and the cleaning pipe are not particularly limited, and are not limited to the longitudinal direction and the circumferential direction (the direction around the central line J) of the sample tube as in the above description. For example, the sample tube and the cleaning pipe may be moved in the radial direction of the sample tube (the direction orthogonal to the longitudinal direction of the sample tube). As described above, when the sample tube and the cleaning pipe are moved along the longitudinal direction of the sample tube, because the movement is linear, the structure is simple. The sampling valve and the sample extracting device can be manufactured at a low cost.

Further, the specific structure of the moving means for relatively moving the sample tube and the cleaning pipe is not limited. In addition to the above-described air actuator, for example, an electrical driving device such as a motor or a solenoid or the like may be used.

The specific structure of the cleaning pipe is not limited to the above-described structure, and it suffices for the cleaning liquid to be able to flow in from the sample inlet.

For example, the cleaning pipe may be provided at the outer side of the sample tube so as to be separate from and not coaxial with the sample tube. As described above, with the structure in which the cleaning pipe is provided coaxial and integral with the sample tube at the outer side thereof, a sufficient cleaning liquid path can be formed in a smaller space.

The directions in which the cleaning liquid and the compressed air flow are not limited to those described above. The cleaning liquid and the compressed air may flow from the sample outlet to the sample inlet of the sample tube.

The sample extracted by the sampling valve and the sample extracting device is not limited to a liquid sample as described above, and the sample may be a gas for example. In other words, if the sample is a fluid, the sampling valve and the sample extracting device of the present invention can be used. Further, the sample may be a solid (such as a fine powder) provided that it can be sucked by the suction device or the pump.

What is claimed is:

1. A device for extracting a sample from a container, the device comprising:
   (a) a cleaning tube;
   (b) a sample tube having an opening, the sample tube being switchably mounted to the cleaning tube, between a sampling position at which the sample tube opening is placed in fluid communication with the environment for contacting a sample in a container, and a cleaning position at which the opening is placed in fluid communication with the cleaning tube for cleaning the sample tube,
   wherein the sample tube includes opposite ends, with the opening formed in one end, and another opening formed in the other end, and
   (c) a means for discharging each of the sample and cleaning agent through said another opening when the device is operated.

2. The device of claim 1, wherein the sample tube and cleaning tube are movable relative to one another along a longitudinal direction of the sample tube.

3. The device of claim 1, wherein the cleaning tube is disposed substantially coaxially with the sample tube.

4. The device of claim 3, wherein the cleaning tube is disposed at an outer side of the sample tube.

5. The device of claim 3, wherein the sample tube and the cleaning tube are rotatable relative to one another.

6. The device of claim 1, wherein the device is for use with a cleaning agent, the device further comprising a cleaning agent supplying device connected in fluid communication to the cleaning tube to supply a cleaning agent to the cleaning tube.

7. A device for introducing an additive to a sample in a container, the device comprising:
   (a) a reservoir for holding an additive for introduction to a sample in a container;
   (b) a cleaning tube;
   (c) a sample tube connected in fluid communication to the reservoir, the sample tube having an opening and being switchably mounted to the cleaning tube, between an adding position at which the opening of the sample tube is placed in fluid communication with the environment for introducing the additive to the sample, and a cleaning position at which the opening is placed in fluid communication with the cleaning tube for cleaning the sample tube,
   wherein the sample tube includes opposite ends, with the opening formed in one end, and another opening formed in the other end, and
   (d) means for discharging each of said cleaning agent and sample through said another opening when the device is operated.

8. The device of claim 7, further comprising an additive supplying device for causing the additive to flow from the reservoir into the sample tube.

9. The device of claim 8, wherein the cleaning tube is disposed at an outer side of the sample tube.

10. The device of claim 8, wherein the sample tube and the cleaning tube are rotatable relative to one another.

11. The device of claim 7, wherein the sample tube includes opposite ends, with the opening disposed in one end, and another opening disposed in the other end.

12. The device of claim 7, wherein the sample tube and cleaning tube are movable relative to one another along a longitudinal direction of the sample tube.

13. The device of claim 7, wherein the cleaning tube is disposed substantially coaxially with the sample tube.

14. The device of claim 7, wherein the device is for use with a cleaning agent, the device further comprising a cleaning agent supplying device connected in fluid communication to the cleaning tube for supplying cleaning agent to the cleaning tube.

15. A method of extracting a sample, comprising the steps of:
   (a) supplying a sample to a sample tube through a first sample tube opening;
   (b) discharging the sample from the sample tube through a second sample tube opening;
   (c) connecting the first sample tube opening to a cleaning tube by moving the sample tube and cleaning tube relative to one another, the sample tube being switchably mounted to the cleaning tube between a sampling position at which the first sample tube opening in placed in fluid communication with the environment for contacting the sample in the container, and a cleaning position at which the first sample tube opening is placed in fluid communication with the cleaning tube for cleaning the sample tube;
   (d) supplying a cleaning agent to the sample tube from the cleaning tube through the first sample tube opening; and
   (e) discharging the cleaning agent from the sample tube through the second sample tube opening.

16. The method of claim 15, further comprising the step of supplying air from the cleaning tube to the first sample tube opening, which is discharged through the second sample tube opening, after the step of supplying a cleaning agent.

17. The method of claim 15, wherein the sample tube has opposite ends, with the first sample tube opening provided at one end, and the second sample tube opening provided at the other end.

18. The method of claim 15, wherein the cleaning tube is provided coaxially with the sample tube at an outer side of the sample tube.

19. The method of claim 15, further comprising the step of repeating said steps (a) through (e).

20. A device for extracting a sample from a container, the device comprising:
   (a) a cleaning tube;
   (b) a sample tube having an opening, the sample tube being switchably mounted to the cleaning tube, between a sampling position at which the sample tube opening is placed in fluid communication with the environment for contacting a sample in a container, and a cleaning position at which the opening is placed in fluid communication with the cleaning tube for cleaning the sample tube, wherein the sample tube includes opposite ends, with the opening formed in one end, and another opening formed in the other end, and (c) means for discharging each of said cleaning agent and said sample through said another opening including a valve in communication with said another opening.

* * * * *